United States Patent
Vanoppen et al.

(10) Patent No.: US 7,220,888 B2
(45) Date of Patent: May 22, 2007

(54) METHOD FOR PRODUCING HYDROCARBONS HAVING A MODIFIED CARBON SKELETON

(75) Inventors: Dominic Vanoppen, Schifferstadt (DE); Ekkehard Schwab, Neustadt (DE); Jean-Marie Basset, Caluire (FR); Jean Thivolle-Cazat, Fontaine sur Saone (FR); Mostapha Taoufik, Rillieux la Pape (FR); Michael Schulz, Worms (DE); Arthur Höhn, Kirchheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 272 days.

(21) Appl. No.: 10/451,739

(22) PCT Filed: Jan. 5, 2002

(86) PCT No.: PCT/EP02/00054

§ 371 (c)(1),
(2), (4) Date: Jun. 25, 2003

(87) PCT Pub. No.: WO02/053520

PCT Pub. Date: Jul. 11, 2002

(65) Prior Publication Data

US 2004/0059169 A1    Mar. 25, 2004

(30) Foreign Application Priority Data

Jan. 8, 2001   (DE) .............................. 101 00 485

(51) Int. Cl.
   *C07C 6/08*   (2006.01)
(52) U.S. Cl. ...................... 585/708; 585/470; 585/646
(58) Field of Classification Search ................ 585/470, 585/708, 646
   See application file for complete search history.

(56) References Cited

U.S. PATENT DOCUMENTS

| 5,177,276 A | * | 1/1993 | Beach et al. .................... 585/7 |
| 5,414,184 A | | 5/1995 | Wu et al. |
| 6,229,060 B1 | * | 5/2001 | Vidal et al. ................. 585/708 |

FOREIGN PATENT DOCUMENTS

| GB | 858649 | | 1/1961 |
| GB | 858649 | * | 11/1961 |
| WO | WO-98/02244 | * | 1/1998 |

* cited by examiner

*Primary Examiner*—Thuan Dinh Dang
(74) *Attorney, Agent, or Firm*—Novak Druce & Quigg, LLP

(57) ABSTRACT

The invention relates to a method for producing hydrocarbons having a modified carbon skeleton by reacting aliphatic hydrocarbons a) with themselves, b) with another aliphatic hydrocarbon or c) with aromatic alkyl substituted hydrocarbons, in the presence of a metal organic catalyst or the hybrid thereof, at a temperature of between 20–400° C. and a pressure of between 0.2–100 bars, wherein the reaction takes place in the presence of hydrogen.

6 Claims, No Drawings

METHOD FOR PRODUCING HYDROCARBONS HAVING A MODIFIED CARBON SKELETON

The present invention relates to a process for preparing hydrocarbons having an altered carbon skeleton in the presence of hydrogen.

WO-A-98/02244 discloses a process for altering aliphatic hydrocarbon chains. Catalysts described are materials in which the active center is the hydride of an element of group 5 or 6 of the Periodic Table of the Elements on a solid support. Even in the simple disproportionation of propane, the activity of the catalyst system is very low. Thus, only 43 catalytic cycles per active center take place over a period of 43 hours.

WO-A-00/27781 discloses the cross-metathesis of an alkane using a catalyst in which an alkyl, alkylidene or alkylidyne radical is bound to an element of group 5 or 6 of the Periodic Table of the Elements on a solid support.

The abovementioned processes leave something to be desired, since the catalysts are rapidly deactivated.

It is an object of the present invention to remedy the abovementioned disadvantage.

We have found that this object is achieved by a new and improved process for preparing hydrocarbons having an altered carbon skeleton by reacting aliphatic hydrocarbons
a) with themselves,
b) with another aliphatic hydrocarbon or
c) with aromatic alkyl-substituted hydrocarbons, at from 20 to 400° C. and a pressure of from 0.2 to 100 bar in the presence of an organometallic catalyst or hydride thereof and in the presence of hydrogen.

In particular, we have found a new and improved process for preparing hydrocarbons having an altered carbon skeleton, wherein hydrocarbons having an altered carbon skeleton of the formula I

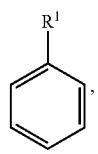

(I)

where
$R^1$ is $C_2$–$C_{20}$-alkyl, are obtained by reacting aliphatic hydrocarbons of the formula III $R^1$—H with aromatic alkyl-substituted hydrocarbons of the formula II

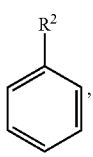

(II)

where
$R^2$ is $C_1$–$C_4$-alkyl, with the proviso that the alkyl radical $R^2$ has a lower or, in the case of a different degree of branching, the same number of carbon atoms than/as the alkyl radical $R^1$.

The process of the present invention can be carried out as follows:

a) Reaction of aliphatic hydrocarbons with themselves (disproportionation):

The aliphatic hydrocarbon III [$R^1$—H] and hydrogen can be reacted at from 20 to 400° C., preferably from 80 to 350° C., particularly preferably from 110 to 280° C., and a pressure of from 0.2 to 100 bar, preferably from 1 to 30 bar, particularly preferably from 3 to 20 bar, in particular from 5 to 15 bar, in the presence of an organometallic catalyst or hydride thereof IV [$L_x$—M—$R^3_{n+q}$]—$H_{1-q}$.

b) Reaction of aliphatic hydrocarbons with another aliphatic hydrocarbon:

The aliphatic hydrocarbon III [$R^1$—H], another aliphatic hydrocarbon III' [$R^{1'}$—H] and hydrogen can be reacted at from 20 to 400° C., preferably from 80 to 350° C., particularly preferably from 110 to 280° C., and a pressure of from 0.2 to 100 bar, preferably from 1 to 30 bar, particularly preferably from 3 to 20 bar, in particular from 5 to 15 bar, in the presence of an organometallic catalyst or hydride thereof IV [$L_x$—M—$R^3_{n+q}$]—$H_{1-q}$.

The molar ratio of aliphatic hydrocarbon III to aliphatic hydrocarbon III' can vary within wide limits; they are generally used in a molar ratio of from 0.7:1 to 50:1, preferably from 0.8:1 to 10:1, particularly preferably from 0.9:1 to 3:1, in particular from 1:1 to 1.5:1.

c) Reaction of aliphatic hydrocarbons with aromatic alkyl-substituted hydrocarbons:

The aromatic alkyl-substituted hydrocarbon II can be reacted with mixtures of the aliphatic hydrocarbon III and hydrogen at from 20 to 400° C., preferably from 80 to 350° C., particularly preferably from 110 to 280° C., and a pressure of from 0.2 to 100 bar, preferably from 1 to 30 bar, particularly preferably from 3 to 20 bar, in particular from 5 to 15 bar, in the presence of an organometallic catalyst or hydride thereof IV [$L_x$—M—$R^3_{n+q}$]—$H_{1-q}$.

The molar ratio of aliphatic hydrocarbon III to aromatic alkyl-substituted hydrocarbon II can vary within wide limits; they are generally used in a molar ratio of from 0.7:1 to 50:1, preferably from 0.8:1 to 10:1, particularly preferably from 0.9:1 to 3:1, in particular from 1:1 to 1.5:1.

In the case of gaseous aliphatic hydrocarbons III, the aromatic alkyl-substituted hydrocarbon II can be saturated with a mixture of aliphatic hydrocarbon III and hydrogen.

The molar ratio of hydrogen to the aliphatic hydrocarbon III can likewise vary within wide limits; they are generally used in a molar ratio of from 0.01:1 to 100:1, preferably from 0.9:1 to 30:1, particularly preferably from 1:1 to 10:1. A larger excess of hydrogen is also possible. The hydrogen is preferably introduced continuously during the reaction. The hydrogen can be separated off in a process step following the synthesis and can be recirculated if desired. The process is particularly preferably carried out using a small proportion of hydrogen.

The substituents and indices $R^1$, $R^2$, $R^3$, M, L, n, q and x in the compounds I, II, III, III' and IV having the following meanings:

$R^1$, $R^{1'}$, with the proviso that $R^1$ and $R^{1'}$ are different,
$C_2$–$C_{20}$-alkyl, preferably $C_2$–$C_{12}$-alkyl such as ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl or isododecyl, particularly preferably $C_2$–$C_6$-alkyl such as ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl or sec-hexyl, in particular $C_2$–$C_4$-alkyl such as ethyl, n-propyl, isopropyl, n-butyl, isobutyl, sec-butyl or tert-butyl, very particularly preferably ethyl, $R^2$
  with the proviso that the alkyl radical $R^2$ contains a smaller or, in the case of a different degree of branching, the same number of carbon atoms than/as the alkyl radical of $R^1$ $C_1$–$C_4$-alkyl such as methyl, ethyl, n-propyl, isopropyl, n-butyl, isobutyl, sec-butyl or tert-butyl, preferably methyl or ethyl, particularly preferably methyl, $R^3$
  independently of one another, saturated or unsaturated ligands having from one to twenty carbon atoms which are bound to M via one or more carbon atoms, e.g. at least one δ bond between carbon and M, for example $C_1$–$C_{20}$-alkyl, preferably $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$–$C_5$-alkyl such as methyl, ethyl, n-propyl, isopropyl, n-butyl, isobutyl, sec-butyl, tert-butyl, n-pentyl or neopentyl, $C_2$–$C_{20}$-alkenyl, preferably $C_2$–$C_8$-alkenyl such as vinyl, allyl, but-2-en-1-yl, but-4-en-1-yl, but-4-en-2-yl, pent-2-en-1-yl, 2,2-dimethylpent-1-en-1-yl, $C_2$–$C_{20}$-alkynyl, preferably $C_2$–$C_8$-alkynyl such as ethynyl, $C_3$–$C_{20}$-cycloalkyl, preferably $C_3$–$C_8$-cycloalkyl such as cyclopropyl, cyclobutyl, cyclopentyl, cyclohexyl, cycloheptyl or cyclooctyl, particularly preferably cyclopentyl, cyclohexyl or cyclooctyl, $C_4$–$C_{20}$-alkylcycloalkyl, preferably $C_4$–$C_{12}$-alkylcycloalkyl such as 2-methylcyclopentyl, 3-methylcyclopentyl, 2,3-dimethylcyclopentyl, 2-ethylcyclopentyl, 3-ethylcyclopentyl, 2,3-diethylcyclopentyl, 2-ethyl-3-methylcyclopentyl, 3-ethyl-2-methylcyclopentyl, 2-methylcyclohexyl, 3-methylcyclohexyl, 4-methylcyclohexyl, $C_4$–$C_{20}$-cycloalkylalkyl, preferably $C_4$–$C_{12}$-cycloalkylalkyl such as cyclopentylmethyl, cyclohexylmethyl, cycloheptylmethyl, cyclooctylmethyl, 1-cyclopentylethyl, 1-cyclohexylethyl, 1-cycloheptylethyl, 1-cyclooctylethyl, 2-cyclopentylethyl, 2-cyclohexylethyl, 2-cycloheptylethyl, 2-cyclooctylethyl, or π bonds between carbon and M, for example $C_1$–$C_{20}$-alkylidenes, preferably $C_1$–$C_8$-alkylidenes such as methylidene ($CH_2$=), ethylidene ($CH_3$—CH=), propylidene ($CH_3$—$CH_2$—CH=), neopentylidene ($[CH_3]_3$—C—CH=), allylidene ($CH_2$=CH—CH=), particularly preferably neopentylidene, or $C_2$–$C_{20}$-alkylidynes, preferably $C_2$–$C_8$-alkylidynes such as ethylidyne ($CH_3$—CH≡), propylidyne ($CH_3$—$CH_2$—CH≡), neopentylidyne ($[CH_3]_3$—C—CH≡), allylidyne ($CH_2$=CH—CH≡), particularly preferably neopentylidyne, and additionally, if desired, $C_1$–$C_{20}$-alkoxy, preferably $C_1$–$C_8$-alkoxy such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy or isooctoxy, particularly preferably $C_1$–$C_5$-alkoxy such as methoxy, ethoxy, n-propoxy, isopropoxy, n-butoxy, isobutoxy, sec-butoxy, tert-butoxy, n-pentoxy, isopentoxy, sec-pentoxy or neopentoxy, or halogens such as fluorine, chlorine, bromine or iodine, preferably fluorine, chlorine or bromine, particularly preferably chlorine or bromine, M a metal of group IIIb, IVb, Vb, VIb, the lanthanides of the Periodic Table of the Elements, magnesium, zinc, cadmium, e.g. scandium, yttrium, lanthanum, actinium, titanium, zirconium, hafnium, vanadium, niobium, tantalum, chromium, molybdenum, tungsten, cerium, praseodymium, neodymium, samarium or a mixture thereof, preferably scandium, yttrium, lanthanum, titanium, zirconium, hafnium, vanadium, niobium, tantalum, chromium, molybdenum, tungsten, cerium or a mixture thereof, particularly preferably titanium, zirconium, hafnium, vanadium, niobium, tantalum, chromium, molybdenum or tungsten, in particular zirconium, tantalum, tungsten or mixtures thereof, L independently of one another, a ligand selected from the group consisting of dialkyl ethers, for example $C_2$–$C_{20}$-dialkyl ethers such as dimethyl ether, ethyl methyl ether, diethyl ether, methyl propyl ether, ethyl propyl ether, dipropyl ether and methyl tert-butyl ether, preferably dimethyl ether and diethyl ether, particularly preferably dimethyl ether, phosphines, for example aromatic, aromatic-aliphatic or aliphatic phosphines such as trimethylphosphine, triethylphosphine, dimethylethylphosphine, diethylmethylphosphine, triphenylphosphine, dimethylphenylphosphine and diphenylmethylphosphine, preferably trimethylphosphine, triethylphosphine and triphenylphosphine, particularly preferably trimethylphosphine, tertiary amines, for example $C_3$–$C_{30}$-tert-amines such as trimethylamine, triethylamine, tripropylamine and triphenylamine, preferably trimethylamine and triethylamine, particularly preferably trimethylamine, and halogens, for example fluorine, chlorine, bromine and iodine, preferably chlorine and bromine, particularly preferably chlorine, n an integer-which is less than or equal to the valence of M, i.e. greater than the lowest oxidation state of 0 up to the maximum oxidation state of M, and in the case of chromium and niobium is preferably 4, 5 or 6, in the case of molybdenum and tungsten is preferably 3, 4, 5 or 6, in the case of vanadium is preferably 4 or 5 and in the case of tantalum is 3 or 5, q an integer from 0 to 1, x an integer from 0 to n, preferably 0, 1 or 2, particularly preferably 0 or 1.

The catalysts can be used as such or preferably on a support. Suitable supports are generally inorganic supports, in particular inert supports, among which oxides, sulfides or mixtures thereof are preferred. Particular preference is given to oxides or mixtures thereof such as silicon dioxide, aluminum oxide, zeolites, natural or synthetic clay minerals, aluminum silicates, titanium dioxides, magnesium oxide, niobium oxide, zirconium oxide or mixtures thereof. Particularly useful supports are porous and nonporous silicalites and aluminates, for example mesoporous silicalites and aluminates having a mean pore diameter of from 20 to 200 Å.

The preparation of the organometallic catalysts or hydrides thereof IV $[L_x$—M—$R^3_{n+q}]$—$H_{1-q}$ is known from WO-A-98/02244 and WO-A-00/27781. In the case of the hydrides IV, the hydrogen is generally present in covalently bound form.

EXAMPLES

The preparation of the catalysts described in the following examples starts out from tris(neopentyl)(neopentylidene) tantalum (TaNp'Np$_3$), which can be obtained by a method published in J. Am. Chem. Soc. 100 (1978), page 3359.

Example 1

Preparation of the catalyst by the sublimation method

Under a protective argon atmosphere, 10 mg of TaNp'Np$_3$ were weighed into a glass vessel equipped with a "break seal" device. The glass vessel was melted off and connected to a second vessel in which SiO$_2$ which had been dehydroxylated at 500° C. was present. After making the reaction vessel inert, the glass membrane between the two vessels was broken and the tantalum complex was sublimed onto the SiO$_2$ support. After the complex had reacted with the support, excess complex was sublimed back. The preparation was treated with hydrogen under slightly subatmospheric pressure. This gave a tantalum hydride immobilized on SiO$_2$. Using the Schlenk technique, toluene and ethane were subsequently introduced into the reaction vessel and reaction to form ethylbenzene was observed.

The species formed on the surface of the SiO$_2$ were characterized by infrared-spectroscopic examination of the samples prepared in this way. However, the sublimation method is also suitable in principle for the preparation of larger amounts of catalyst.

Example 2

Preparation of the catalyst: impregnation method

In the absence of air, 640 mg of tris(neopentyl)neopentylidenetantalum were dissolved in dry (water-free) pentane, reacted at room temperature with 3 g of SiO$_2$ which had been dehydroxylated at 500° C. (Degussa, Aerosil, 200 m$^2$/g), filtered off and exposed to a hydrogen atmosphere at 150° C. under a slightly subatmospheric pressure of 0.9 bar.

Example 3

Continuous reaction of toluene with ethane in the presence of hydrogen

The ethane/hydrogen mixture was saturated with toluene in a molar ratio of 10:1 and subsequently reacted over 400 mg of the catalyst prepared in Example 2 in a flow-through reactor at 250° C. and a total pressure of 1 bar. The composition of the reaction products was determined by gas chromatography and the yield of ethylbenzene was expressed as a ratio to the amount of tantalum present in the catalyst. The results are shown in Table 1.

Comparative Example A

Continuous Reaction of Toluene with Ethane in the Absence of H$_2$

The procedure of Example 3 was repeated, but the gas mixture passed over the catalyst contained no hydrogen. The results are shown in Table 1.

TABLE 1

| Example No. | Reaction time [h] | Conversion/h* (relative rates) | Yield [mol of ethylbenzene/ mol of tantalum] |
|---|---|---|---|
| 3 | 70 | 8 | 3.4 |
| Comparison A | 97 | 1 | 1.95 |

We claim:

1. A process for preparing hydrocarbons having an altered carbon skeleton by reacting aliphatic hydrocarbons of the formula III R$^1$—H
   a.) with themselves,
   b.) with another aliphatic hydrocarbon of the formula III' R$^{1'}$—H or
   c.) with aromatic alkyl-substituted hydrocarbons of the formula II,

(II)

at from 20 to 400° C. and a pressure of from 0.2 to 100 bar in the presence of an organometallic catalyst or hydride thereof and in the presence of hydrogen, where R$^1$ and R$^{1'}$ are different C$_2$–C$_{20}$alkyl-substituents and R$^2$ is C$_1$–C$_4$-alkyl, with the proviso that the alkyl radical R$^2$ has a lower or, in the case of a different degree of branching, the same number of carbon atoms than/as the alkyl radicals R$^1$.

2. A process for preparing hydrocarbons having an altered carbon skeleton as claimed in claim 1, wherein hydrocarbons having an altered carbon skeleton of the formula I

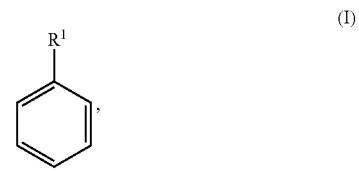

(I)

where
R$^1$ is C$_2$–C$_{20}$-alkyl,
are obtained by reacting aliphatic hydrocarbons of the formula III R$^1$—H with aromatic alkyl-substituted hydrocarbons of the formula II

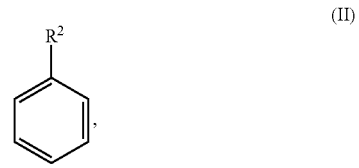

(II)

where

R² is $C_1$–$C_4$-alkyl, with the proviso that the alkyl radical R² has a lower or, in the case of a different degree of branching, the same number of carbon atoms than/as the alkyl radical R¹.

3. A process for preparing hydrocarbons having an altered carbon skeleton as claimed in claim 2, wherein the molar ratio of hydrogen to the aliphatic hydrocarbon III is from 0.01:1 to 100:1.

4. A process for preparing hydrocarbons having an altered carbon skeleton as claimed in claim 1, wherein the organometallic catalyst or hydride thereof used is a compound of the formula IV $[L_x\text{---}M\text{---}R^3{}_{n+q}]\text{---}H_{1-q}$, where M is a metal of group Vb or VIb of the Periodic Table of the Elements, L are each, independently of one another, a ligand selected from the group consisting of dialkyl ethers, phosphines, tertiary amines and halogens, R³ are, independently of one another, saturated or unsaturated ligands having from one to twenty carbon atoms which are bound to M via one or more carbon atoms, n is an integer less than or equal to the valence of M, q is 0 or 1, x is from 0 to n, on a support.

5. A process for preparing hydrocarbons having an altered carbon skeleton as claimed in claim 1, wherein a.) is a disproportionation reaction.

6. A process for preparing hydrocarbons having an altered carbon skeleton as claimed in claim 1, wherein b.) and c.) are metathesis reactions.

* * * * *